United States Patent
Takase

Patent Number: 5,084,013
Date of Patent: Jan. 28, 1992

[54] SUCTION TUBE FOR USE IN SURGICAL OPERATION

[76] Inventor: Haruo Takase, 20-16, Shimoochiai 3-chome, Shinjuku-ku, Tokyo, Japan

[21] Appl. No.: 464,195

[22] Filed: Jan. 12, 1990

[30] Foreign Application Priority Data

Jan. 13, 1989 [JP] Japan .................. 1-2933[U]

[51] Int. Cl.⁵ .............................................. A61M 3/00
[52] U.S. Cl. ................................. 604/43; 604/272
[58] Field of Search ............. 604/22, 27, 35, 204, 604/272-274, 902, 43

[56] References Cited

U.S. PATENT DOCUMENTS

| | | | |
|---|---|---|---|
| 1,114,268 | 10/1914 | Kells | 604/902 X |
| 3,810,471 | 5/1974 | Truhan | 604/902 X |
| 4,002,170 | 1/1977 | Hansen et al. | 604/902 X |
| 4,648,871 | 3/1987 | Jacob | 604/149 |
| 4,650,461 | 3/1987 | Woods | 604/28 |
| 4,690,672 | 9/1987 | Veltrup | 604/43 |
| 4,808,157 | 2/1989 | Coombs | 604/44 |
| 4,861,332 | 8/1989 | Parisi | 604/22 |
| 4,872,837 | 10/1989 | Issalene et al. | 433/29 |
| 4,886,491 | 12/1989 | Parisi et al. | 604/22 |
| 4,913,698 | 4/1990 | Ito et al. | 604/22 |
| 4,958,901 | 9/1990 | Coombs | 604/44 |

*Primary Examiner*—C. Fred Rosenbaum
*Assistant Examiner*—Adam J. Cermak
*Attorney, Agent, or Firm*—Oblon, Spivak, McClelland, Maier & Neustadt

[57] ABSTRACT

A surgical suction tube having a suction mouth open to a different direction from the axis of the tube and a fluid supply tube attached to the outside of the suction tube. With this suction tube, subcutaneous tissues such as fat can be efficiently aspirated by use of an aspirator without needlessly injuring blood vessels, nerve tissues and so on.

3 Claims, 2 Drawing Sheets

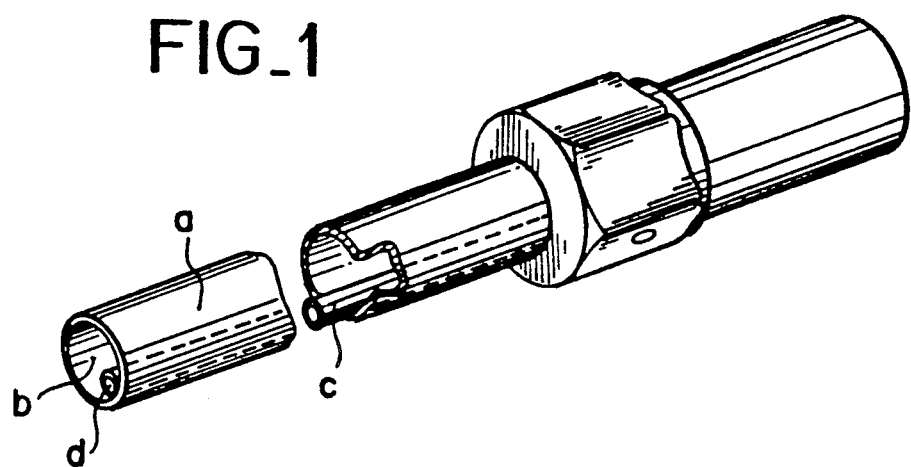
FIG_1
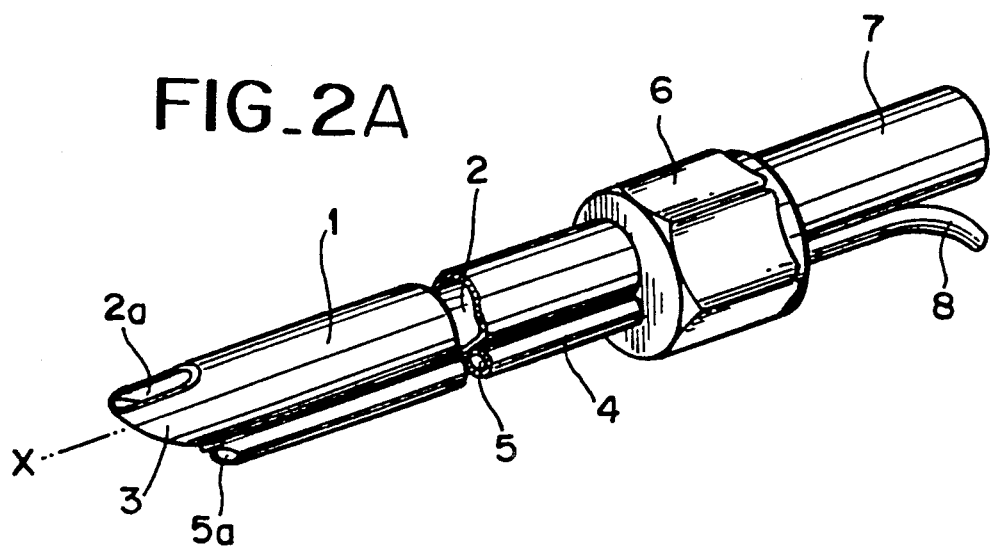
FIG_2A
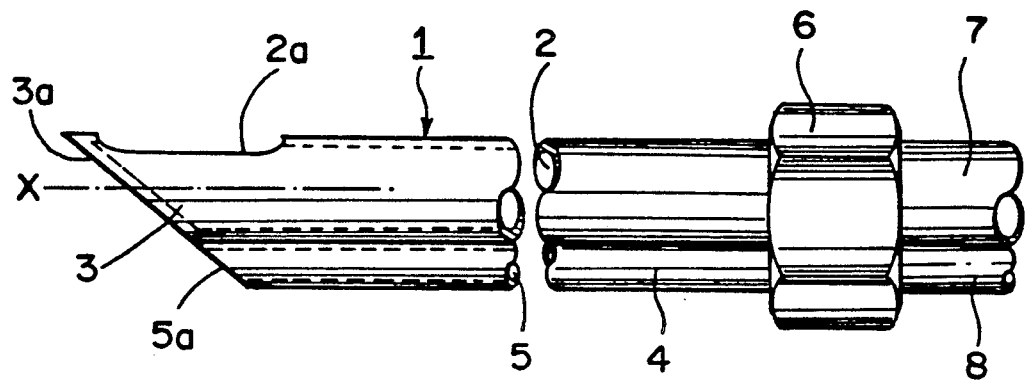
FIG_2B

FIG_3
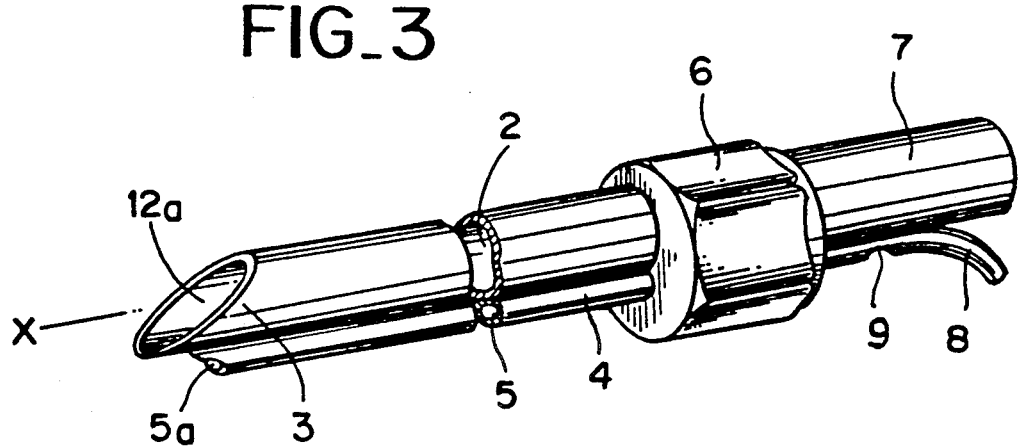
FIG_4
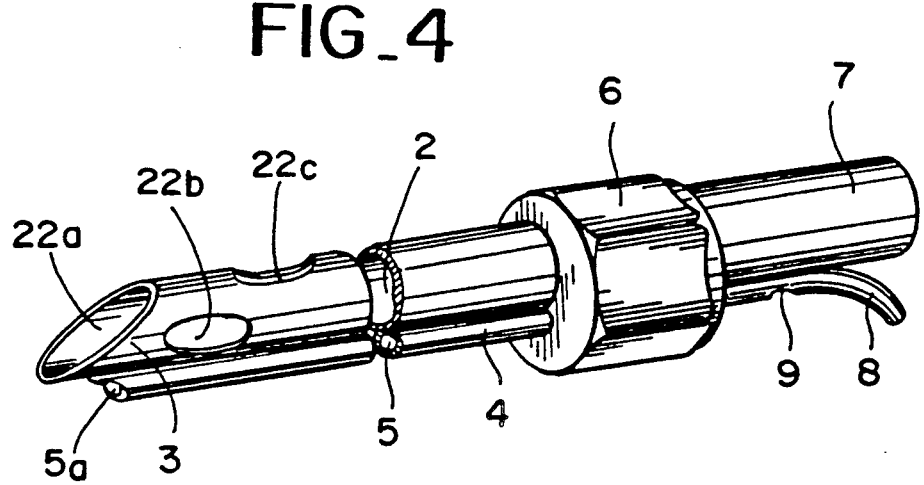
FIG_5
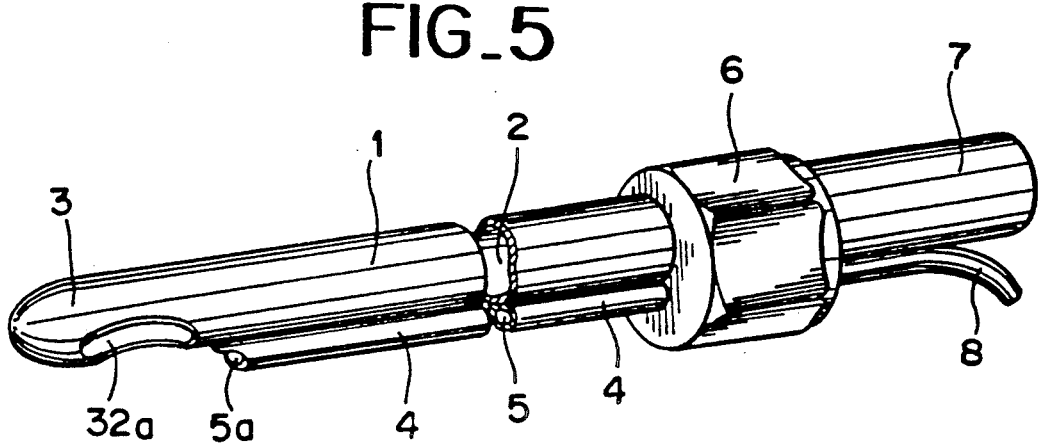

SUCTION TUBE FOR USE IN SURGICAL OPERATION

BACKGROUND OF THE INVENTION

1. Field of the Invention

This invention relates to a suction tube for use in an surgical operation such as plastic surgery which is performed by use of a aspirator for aspirating, for instance, subcutaneous fat, and more particularly to an improvement in and concerning a surgical suction tube with which a surgical operation for fat aspiration can be performed readily and safely and which is expected to reduce the period for healing an operation wound.

2. Description of the Prior Art

There has been conventionally used a suction tube for aspirating subcutaneous fat by use of a fat aspirator, as illustrated in FIG. 1. This suction tube comprises a suction tube body Ts integrally incorporating therein a fluid supply tube Ta having a small diameter. A mouth m formed at the leading end of the suction tube body Ts is open in the axial direction of the suction tube. That is to say, the secant plane defining the mouth m is perpendicular to the axis X of the suction tube body Ts. In the case of using this suction tube in a surgical operation for aspirating subcutaneous fat of the abdomen, the leading end of the suction tube body Ts is first stuck into under the skin through an incision hole formed in the abdominal skin, and thereafter, subcutaneous adipose tissue is aspirated from the mouth m through the suction tube body Ts by means of an external fat aspirator (not shown) connected to the suction tube while intermittently blowing air or some other fluid toward the mouth m through the fluid supply tube Ta.

However, the prior art suction tube having such a structure as noted above is inevitably made relatively large in diameter because it incorporate therein the fluid supply tube Ta. It has been known in the surgical experience that when using such a suction tube having a large diameter, the incision hole formed in the skin is inevitably enlarged, consequently making an incision wound large and indecent, and various problems will possibly be encountered during a surgical operation. Besides, the suction tube body Ts provided inside with the fluid supply tube Ta is thus complicated in structure and difficult to manufacture, inevitably turning out to be expensive.

Moreover, the suction tube body Ts of the conventional suction tube has an inner cross section deformed in a non-circular shape due to the fluid supply tube Ta being disposed inside the suction tube body Ts. Hence, this suction tube entails disadvantages such that the efficiency of aspirating, for example, subcutaneous adipose tissues is lowered and the tube is easily clogged with sucked substances such as subcutaneous fat in a surgical operation.

Besides the problem described above, the conventional suction tube having a relatively large outer diameter and the mouth whose secant plane is perpendicular to the axial direction as mentioned above is possibly intended to aspirate subcutaneous fat more than required and is susceptible to injure blood vessels, nerve tissues and so on.

OBJECT OF THE INVENTION

This invention is made to eliminate the drawbacks suffered by the conventional surgical suction tube and aims at offerring a suction tube capable of being readily inserted into under the skin and lessening injuries done to blood vessels, nerve tissues and so on in a surgical operation.

Another object of the present invention is to provide a surgical suction tube capable of adequately aspirating subcutaneous fat, which is simple in structure and can be manufactured inexpensively.

SUMMARY OF THE INVENTION

To attain the objects described above according to this invention there is provided a surgical suction tube comprising a suction tube body with a head portion having in its leading end portion a suction mouth open in a direction different from the axial direction of the suction tube body, and a fluid supply tube attached onto the outer surface of the suction tube body so as to permit a fluid to be supplied toward around the suction mouth of the suction tube body.

Since the mouth formed at the leading end portion of the suction tube body is open out of the axial direction of the suction tube body, the suction tube can be readily stuck and moved in the subcutaneous tissues to effectively aspirate subcutaneous fat, for example, without needlessly injuring blood vessels, nerve tissues and so on in a surgical operation.

The structure in which the fluid supply tube attached to the outside of the suction tube body has an advantage in that the suction tube body has a circular inner cross section so as to not merely improve the efficiency of aspirating the subcutaneous tissues such as subcutaneous fat, but also prevent the tube from being clogged with the tissues aspirated in the operation for aspiration and to enable the tube to be rinsed with remarkable ease after the surgical operation.

Furthermore, since this suction tube body does not incorporate therein the fluid supply tube, it can be reduced in diameter to any extent according to demand.

As a fluid to be introduced through the fluid supply tube, there can be used not only gas such as air, but also Ringer's solution or other injection fluid.

BRIEF DESCRIPTION OF THE DRAWINGS

The other objects and features of the present invention will now be explained in detail with reference to the accompanying drawings, wherein:

FIG. 1 is a partially cutaway perspective view showing a conventional surgical suction tube;

FIG. 2A and 2B are a partially cutaway perspective view and side view showing a first embodiment of the surgical suction tube according to this invention, respectively;

FIG. 3 is a partially cutaway perspective view showing a second embodiment of the suction tube of the invention;

FIG. 4 is a partially cutaway perspective view showing a third embodiment of the suction tube of the invention; and FIG. 5 is a partially cutaway perspective view showing a fourth embodiment of the suction tube of the invention.

DESCRIPTION OF THE PREFERRED EMBODIMENTS

The preferred embodiments of the surgical suction tube will be described hereinafter with reference to FIGS. 2 through 5. In these drawings, reference numeral 1 denotes a suction tube body, 4 a fluid supply tube, and 6 a base member.

In FIGS. 2A and 2B, there is illustrated the first embodiment of the suction tube according to this invention, which comprises the suction passage 2 and a head portion 3 provided with a leading end 3a formed with a slanted surface with respect to a surface perpendicular to the axis X of the suction tube body 1. That is, in this embodiment, the leading end 3a of the suction tube body is closed in a blind state with the slanted surface. The suction tube body 1 is fixed onto the base member 6.

In the head portion 3, there is formed a suction mouth 2a which is open in a different direction from the direction of the axis X of the suction tube body 1 To be specific, the suction mouth is formed in the circumferential wall of the head portion 3 in such a state that the width direction of the suction mouth 2a is parallel to the axial direction of the suction tube. Namely, the suction mouth 2a is open to the direction perpendicular to the axial direction of the suction tube body 1.

The fluid supply tube 4 having a fluid passage 5 therein is smaller in diameter than the suction tube body 1 and is attached onto the outer circumferential surface of the suction tube body 1. The fluid supply tube 4 extending along the suction tube body 1 is integrally fixed to the suction tube body by welding or using adhesives and supported at its basal end by the base member 6. At the leading end of the fluid supply tube 4, there is formed an injection mouth 5a which opens in a direction different from its axis (i.e., the axes paralled to the axial direction X of the suction tube body 1).

In this embodiment, the direction in which the injection mouth 5 of the fluid supply tube 4 is inclined is substantially equal to that of slanted leading end 3a of the suction tube body 1.

In the drawing, denoted by numeral 7 is conduit means connected with the suction tube body 1 and numeral 8 is conduit means connected with the fluid supply tube 4.

The inclination angle and shape of the suction mouth 2a formed in the head portion 3 of the suction tube body 1 can be modified in various ways.

In the second embodiment illustrated in FIG. 3 the suction tube body 1 has in its leading end a suction mouth 12a inclined at approximately 45° relative to the axial direction of the suction tube body. The injection mouth 5a of the fluid supply tube 4 is inclined symmetrically with respect to the slant suction mouth 12a of the suction tube body.

The fluid supply tube 4 in this embodiment serves to introduce a fluid such as gas, air and a solution. The conduit means 8 connected with the fluid supply tube 4 is provided with a vent hole 9 which vents to atmosphere. During the supply of the fluid as noted above, the amount of the fluid to be injected out of the injection mouth 5a can be regulated by opening or closing the vent hole 9 with a finger. That is to say, the amount of the fluid to be injected is reduced by opening the vent hole 9 or vice versa. On the other hand, in the case of performing a surgical operation by use of the suction tube of the invention without supplying a fluid through the fluid supply tube, the amount of subcutaneous tissues aspirated can be regulated. That is, when the vent hole 9 is closed with a finger in this case so as not to supply a fluid to around the suction mouth 12a, the subcutaneous tissues are strongly aspirated. On the contrary, when opening the vent hole 9, atmosphere flows into the fluid supply tube 4 (passage 5) through the vent hole 9 and is permitted to pass into the suction tube body 1 (passage 2), consequently this reduces the amount of the subcutaneous tissues to be aspirated. The aforenoted vent hole 9 for regulating the amount of the fluid passing through the passage 5 is of course applicable to the former embodiment.

The third embodiment illustrated in FIG. 4 employs one or more auxiliary suction mouths 22b, 22c formed in adequate positions on the circumferential wall of the head portion 3 of the suction tube body 1 in addition to a suction mouth 22a like that in the aforementioned second embodiment. The auxiliary suction mouths 22b, 22c are applicable to the first embodiment illustrated in FIGS. 2A and 2B. With this structure having the auxiliary suction mouths, the efficiency of aspirating subcutaneous fat or the like can be heightened.

In the fourth embodiment illustrated in FIG. 5, a leading end 33a of the suction tube body 1 assumes a substantially elliptical cone shape. The suction tube body 1 has a suction mouth 32a which is formed on the side onto which the fluid supply tube 4 is attached, so as to open opposite to the fluid supply mouth 5a.

The structure of the suction mouth and the leading end configurations of the suction tube body described above in accordance with the aforementioned embodiments may be modified and combined in various ways. Preparation of the suction tubes of various types according to the aforenoted embodiments will serve to facilitate performance of a surgical operation.

In a case of using any of the suction tubes of the foregoing embodiments for performing a surgical operation, the conduit means 7 of the suction tube body 1 and the conduit means 8 of the fluid supply tube 4 are connected to an aspirator (not shown) or any other apparatuses through respective hoses. The head portion 3 of the suction tube body is stuck into subcutaneous tissues through the skin while intermittently supplying air or Ringer's solution through the fluid supply tube 4. Simultaneously, the subcutaneous tissue such as fat is aspirated from the suction mouth through the suction tube body 1. The tissue thus aspirated is fed to the aspirator through the conduit means 7 by suction.

If a known vibrator such as a piezoelectric vibrator is provided on the head portion 3 of the suction tube, subcutaneous cells or tissues such as fat can be destroyed so as to be emulsified, and consequently be aspirated with notably high efficiency.

As is evident from the foregoing, according to this invention, there can be provided a surgical suction tube excellent in the ability to aspirate subcutaneous tissues such as fat. Namely, the suction tube of the invention is provided with a suction mouth which is open in a direction different from the axial direction of the suction tube so that the subcutaneous tissues to be removed can be adequately aspirated with ease without needlessly injuring blood vessels and nerve tissues. Besides, since a fluid supply tube is integrally attached to the outside of the suction tube body, the suction tube including the fluid supply tube can be entirely reduced in size in comparison with prior art suction tubes. As such, the suction passage inside the suction tube body has a substantially circular cross section, so that the efficiency of aspirating subcutaneous tissues can be remarkably heightened and otherwise possible problems of clogging the suction tube with the tissues aspirated can be eliminated. In addition, the suction tube can be easily rinsed after a surgical operation and can be manufactured inexpensively because it is simple in structure.

As can be readily appreciated, it is possible to deviate from the above embodiment of the present invention and, as will be readily understood by those skilled in this art, the invention is capable of many modifications and improvements within the scope and spirit thereof. Accordingly, it will be understood that the invention is not to be limited by these specific embodiments, but only by the scope and spirit of the appended claims.

What is claimed is:

1. A surgical suction tube which comprises:
   a suction tube body having an inclined leading end in which a suction mount is formed which opens in a direction different from an axial direction of said suction tube body;
   a fluid supply tube attached outside said suction tube body extending parallel to said suction tube body and having an injection mouth outside of said suction mouth which opens in a direction different from that in which said suction tube body opens, so as to supply a fluid therethrough to a position around said suction mouth of said suction tube body, said injection mouth of said fluid supply tube being inclined, away from and symmetric with respect to the slanted suction mouth of said suction tube body.

2. A surgical suction tube which comprises:
   a suction tube body having a leading end with a suction mouth which opens in a direction which is inclined from an axial direction of said suction tube body and having an injection mouth which opens in the direction opposite to said inclined leading end of said suction tube body, so as to supply a fluid therethrough to around said suction mouth of said suction tube body, said injection mouth of said fluid supply tube being inclined away from and symmetric with respect to the inclined suction mouth of said suction tube body.

3. A surgical suction tube which comprises:
   a suction tube body having an inclined leading end with a suction mouth which opens in a direction different from an axial direction of said suction tube body,
   a fluid supply tube attached outside said suction tube body, extending parallel to said suction tube body and having an injection mouth outside of said suction mouth and extending in a direction different from the axial direction thereof, so as to supply a fluid therethrough to a position around said suction mouth of said suction tube body, and
   conduit means connected to said fluid supply tube which is provided with a vent hole which vents to atmosphere for regulating an amount of a fluid to be fed to said fluid supply tube.

* * * * *